US011246764B2

(12) United States Patent
Biddulph et al.

(10) Patent No.: US 11,246,764 B2
(45) Date of Patent: Feb. 15, 2022

(54) COMPRESSION GARMENT HAVING ENHANCED STRAP CONFIGURATION

(71) Applicant: Julius Zorn, Inc., Cuyahoga Falls, OH (US)

(72) Inventors: Greg Biddulph, Cuyahoga Falls, OH (US); Carla J. Blackman, Cuyahoga Falls, OH (US); Douglas R. Halley, Cuyahoga Falls, OH (US); Adrian Slattery, Cuyahoga Falls, OH (US)

(73) Assignee: Julius Zom, Inc., Cuyahoga Falls, OH (US)

( * ) Notice: Subject to any disclaimer, the term of this patent is extended or adjusted under 35 U.S.C. 154(b) by 979 days.

(21) Appl. No.: 15/580,840

(22) PCT Filed: Jun. 14, 2016

(86) PCT No.: PCT/US2016/037339
§ 371 (c)(1),
(2) Date: Dec. 8, 2017

(87) PCT Pub. No.: WO2016/205179
PCT Pub. Date: Dec. 22, 2016

(65) Prior Publication Data
US 2018/0338868 A1    Nov. 29, 2018

Related U.S. Application Data

(60) Provisional application No. 62/181,560, filed on Jun. 18, 2015.

(51) Int. Cl.
*A61F 13/08* (2006.01)
*A61F 13/00* (2006.01)

(52) U.S. Cl.
CPC .. *A61F 13/085* (2013.01); *A61F 2013/00127* (2013.01); *A61F 2013/00153* (2013.01)

(58) Field of Classification Search
CPC .... A61F 13/06–148; A61F 2013/00089; A61F 2013/00119–00153;
(Continued)

(56) References Cited

U.S. PATENT DOCUMENTS 2,574,678 A  *  11/1951  Wilbur ..................... A61F 5/03
                                                    2/301
3,327,394 A       3/1965  Tenteris
(Continued)

FOREIGN PATENT DOCUMENTS

| EP | 2436350 | 4/2012 |
|----|---------|--------|
| WO | WO 2000015139 | 3/2000 |
| WO | WO 2010025186 | 3/2010 |

OTHER PUBLICATIONS

International Search Report of PCT/US2016/037339 dated Dec. 15, 2016, 6 pages.
(Continued)

*Primary Examiner* — Michelle J Lee
(74) *Attorney, Agent, or Firm* — Renner, Otto, Boisselle & Sklar, LLP

(57) ABSTRACT

A low-elastic compression garment includes a central main portion and multiple straps that extend laterally from the central main portion. Notches may be provided where the straps meet the central main portion, and may be formed into the central main portion adjacent to respective straps. With the notches, when the compression garment is in a wrapped position, lateral edges of adjacent straps that are associated with the notches overlap without gaps or bunching of the strap material. The compression garment may include distal and proximal counter pull tabs that extend from opposite edges of the central main portion. When the distal and proximal counter pull tabs are pulled by the user, pulling forces are transmitted in opposing directions to tension the straps. A removable fastening tab is provided respectively at
(Continued)

ends of each of the straps. The fastening tabs are repositionable at different locations on the straps, resulting in a compression garment that is both reversible and easily sized for a customized fit.

7 Claims, 8 Drawing Sheets

(58) Field of Classification Search
CPC .............. A61F 5/01–0118; A61F 5/02–03; A61F 7/02; A61F 7/08; A61F 7/10; A61F 7/106; A61F 2007/0225; A61F 2007/0228–0231; A61F 2007/108
See application file for complete search history.

(56) References Cited

U.S. PATENT DOCUMENTS

| | | | |
|---|---|---|---|
| 3,935,858 A * | 2/1976 | Harroff | A61F 5/0109 |
| | | | 602/26 |
| 5,221,252 A * | 6/1993 | Caprio, Jr. | A61F 5/0106 |
| | | | 602/26 |
| 5,865,777 A * | 2/1999 | Detty | A61F 5/0109 |
| | | | 602/26 |
| 7,329,232 B2 | 2/2008 | Lipshaw et al. | |
| 7,942,838 B2 | 5/2011 | Farrow | |
| 8,007,454 B1 * | 8/2011 | Zerr | A61F 5/0111 |
| | | | 602/23 |
| 8,663,144 B2 | 3/2014 | Farrow et al. | |
| 8,747,341 B2 | 6/2014 | Farrow et al. | |
| 2003/0149389 A1 | 8/2003 | Daneshvar | |
| 2005/0192524 A1 | 9/2005 | Lipshaw et al. | |
| 2007/0282232 A1 | 12/2007 | Hoffman | |
| 2010/0292622 A1 * | 11/2010 | Weissleder | A61F 5/0193 |
| | | | 602/23 |
| 2010/0312160 A1 | 12/2010 | Creighton et al. | |
| 2011/0087145 A1 * | 4/2011 | Farrow | A61F 5/0118 |
| | | | 602/22 |
| 2012/0179084 A1 | 7/2012 | Lipshaw et al. | |
| 2015/0025424 A1 | 1/2015 | Richardson et al. | |

OTHER PUBLICATIONS

Written Opinion of the International Searching Authority of PCT/US2016/037339 dated Dec. 15, 2016, 15 pages.

* cited by examiner

COMPRESSION GARMENT HAVING ENHANCED STRAP CONFIGURATION

RELATED APPLICATIONS

This application is national stage application pursuant to 35 U.S.C. § 371 of PCT/US2016/037339 filed on Jun. 14, 1967, which claims the benefit of U.S. Provisional Application No. 62/181,560 filed Jun. 18, 2015, the contents of which are incorporated herein by reference.

FIELD OF INVENTION

The present invention relates to therapeutic compression garments worn to prevent fluid build-up in the limbs, and particularly relates to compression garments having straps that wrap around a patient's limb.

BACKGROUND OF THE INVENTION

Therapeutic compression garments are worn to prevent the build-up of fluid in the limbs, a condition commonly referred to as edema and various types of vascular insufficiencies. Persons who may use such a garment include post-surgical patients, obese persons, and persons with ailments that impede circulation, such as Chronic Venous Insufficiency, Lymphedema and diabetics. Compression garments improve circulation and prevent fluid from collecting in the lower limb portions, such as in the feet and ankles (leg compression garment) or hands (arm compression garment). By improving circulation and reducing the propensity toward fluid build-up, compression garments relieve swelling and associated pain, prevent and help in the treatment of ulcers, and prevent other issues that can result from poor circulation in the limbs.

Various types of compression garments are known in the art. One type of compression garment is a tubular shaped, high elastic, knitted compression garment, which provides graduated compression when worn on a limb. High elastic compression garments offer only a minimal increase in working pressure allowing them to be easier to don. Depending upon the level of a patient's clinical involvement, such garments may, at times, not provide an adequate level of pressure to improve circulation or prevent edema in the limb.

Accordingly, more "low-elastic", stretch-limited compression garments also have been used to provide compression, but such garments likewise must be able to accommodate changes in compression based on changes in the size of the limb. Low-elastic garments have an advantage over elastic garments in that low elastic garments provide an increased or higher working pressure in response to increased patient activity or limb edema. As a limb expands due to muscle expansion or edema, the expanded limb pushes up against the low-elastic garment, which is stretch-limited and therefore offers greater resistance as compared to high-elastic garments. This results in higher working pressure. The relatively high working pressure of low-elastic garments results in an improved vascular flow and edema containment. As a consequence of the high working pressure and limited stretch, low-elastic garments formed in a tubular shape can be considerably more difficult to don as compared to high-elastic garments.

To provide for a more dynamic compression that adjusts with changing situations and are easier to don, wrap-style low-elastic compression garments have been employed. Such garments may be wrapped around a limb and secured using a fastening device, such as a hook and loop mechanical fastening device. As such, they may be removed and re-wrapped with differing tensions to accommodate any changing compression needs. Wrapped compression garments may be configured with staggered compression straps or bands that are linked together by a central spine or region, the straps wrapping around the limb. The use of bands or straps provides substantial versatility in achieving a desired amount of compression, both as therapeutically required and to provide a more comfortable fit.

Conventional low-elastic wrapped compression garments with bands or straps, however, still have deficiencies related to providing a desired fit. It is desirable that there not be significant gaps between the straps in use. Any significant gaps constitute areas where compression is not applied, and thus provide areas where fluid may accumulate. This can result in limb tissue bulging between the bands, which reduces the effectiveness of the compression and may result in discomfort. One option to avoid problems associated with gaps is to configure the bands so that they essentially are touching with minimal overlap, but in use, with patients being of different sizes and with movement, it is difficult to create a single product that could accommodate a wide range of limb sizes while maintaining a gapless configuration.

Another option is to have the bands overlap, but overlapping bands can bunch up, particularly where the bands connect to the spine or central region. To provide high working pressure as referenced above without gaps, conventional configurations may overlap the bands by as much as 50%. This provides a bulky configuration that requires a significant amount of material to manufacture, and the bulkiness could result in discomfort to the user.

Another deficiency of conventional low-elastic compression garments pertains to providing versatility of size to accommodate various sized patients. To reduce manufacturing costs and complexity, and reduce the need for maintaining a large and varied inventory, it is desirable that a given compression garment be able to accommodate multiple sizes of patients. This reduces the number of different configurations that must be maintained by an end user facility, such as a hospital or nursing home. Various sizing schemes, such as markings and other indicators, have been employed to aid in cutting the straps down to appropriate sizes, but such systems often are complicated and prone to user error.

A related deficiency of conventional low-elastic compression garments is that wrapped compression garments can be difficult to don with sufficient compression. Users often are elderly or infirmed, and the force required to pull the bands or straps tight to the desired level of compression can be difficult for such users to apply. The result may be a donning with inadequate compression, and in turn a resultant inadequate therapeutic performance.

In view of the above deficiencies, conventional low-elastic compression garments are not being utilized to their maximum potential.

SUMMARY OF THE INVENTION

The present invention provides an enhanced low-elastic wrap compression garment that improves over the deficiencies of conventional compression garments. In exemplary embodiments, a low-elastic wrap compression garment may be formed of two halves that are sewn together at a central seam. Each half includes a half main portion and a plurality of straps that extend from the half main portion. Straps may extend from each half main portion. The two half main portions are sewn together, thereby forming a stitched central seam. For wrapping around certain limbs, like the calf, the seam may be configured to provide a biased curvature so that the completed garment has a contour that is intended to be commensurate with a typical limb shape, such as for example a shape of a patient's calf. For limbs in which the curvature is larger and more uniform, such as the thigh, the garment may be formed with a unitary component including a main portion from which the plurality of straps extend.

The straps are staggered such that when the straps are wrapped around the remainder of the limb, there is an overlap of the lateral edges of the straps in the wrapping around direction. The garment may have a notched configuration to enhance the overlapping nature of the straps. In one exemplary embodiment, where each strap extends from the respective half main portion or a unitary main portion, a notch is provided so that adjacent straps may overlap to provide a gapless configuration, without bunching of the strap material. The notch permits a minimal overlap of less than about ¼ inch and as little and ⅛ inch. In another exemplary embodiment, a concave curvature may be formed in the half main portion or unitary main portion between the straps, and the notches are provided within the concave curvature adjacent to where a strap extends from the main portion. In another exemplary embodiment, the notches may be configured as shaped recesses formed extending into the half main portion or unitary main portion adjacent to where a strap extends from the main portion. Distal and proximal counter pull tabs may be provided on each half main portion or in a unitary main portion, which aids the user in putting tension on the distal and proximal straps to aid in donning the compression garment with the desired level of compression.

The compression garment further may include woven fabric layers of different colors. Removable fastening tabs may be provided that are removable from the straps to permit reversibility of the compression garment such that either color may be visible. In addition, positioning the removable fastening tabs at different locations along the straps provides a marker for cutting the straps to any suitable size for a customized fit. Accordingly, a wide range of user sizes may be accommodated with a single compression garment.

An aspect of the invention, therefore, is a low-elastic wrap compression garment. In exemplary embodiments, the low-elastic compression garment includes a central main portion including a plurality of longitudinal outer edges, a plurality of straps that extend laterally from the longitudinal outer edges of the central main portion, each of the plurality of straps having opposite lateral edges, and an end that attaches to the central main portion adjacent an opposite longitudinal outer edge in use, and at least one notch where a lateral edge of one of the straps meets one of the longitudinal outer edges of the central main portion. When the compression garment is in a wrapped position, lateral edges of adjacent straps that are associated with the at least one notch can overlap. The at least one notch may be configured as a plurality of notches. A notch may be provided adjacent to where a lateral edge of one of the straps meets one of the longitudinal outer edges of the central main portion, wherever a lateral edge of one of the straps overlaps a lateral edge of an adjacent strap when the compression garment is in the wrapped position.

In another exemplary embodiment, the central main portion may be formed of two half main portions sewn together with a biased seam that has a three-dimensional curvature for form fitting to the curvature of a limb portion.

In another exemplary embodiment, the central main portion may include a concave curvature extending between straps, and the notches are provided within the concave curvature adjacent to where a strap extends from the main portion. In another exemplary embodiment, the notches may be configured as shaped recesses formed extending into the central main portion adjacent to where a strap extends from the main portion.

In exemplary embodiments of the low-elastic compression garment, the central main portion includes first and second opposite lateral outer edges that extend substantially perpendicularly relative to the longitudinal outer edges. The compression garment further may include a distal counter pull tab that extends from the first lateral outer edge of the central main portion, and a proximal counter pull tab that extends from the second lateral outer edge of the central main portion. When the distal and proximal counter pull tabs are pulled by the user, pulling forces are transmitted in opposing directions to tension the straps.

In exemplary embodiments of the low-elastic compression garment, each of the plurality of straps has an end that is remote from where the strap meets the longitudinal outer edge of the central main portion. A plurality of fastening tabs respectively may be provided at each of the ends of the straps, wherein each fastening tab is removable from a respective strap and repositionable at a different location on the respective strap. The ability to remove and reposition the fastening tabs results in a compression garment that is both reversible for different colors, and easily adjusted for a more customized fit.

Another aspect of the invention is a method of fitting a low-elastic compression garment that is wrapped around a limb of a user. In exemplary embodiments, the fitting method may include the steps of providing a low-elastic compression garment (for example a compression garment in accordance with any of the embodiments disclosed herein), removing at least one fastening tab from a respective strap, and repositioning the fastening tab at a different location on the respective strap.

The fitting method may include repositioning at least one fastening tab laterally on a same side of the respective strap, wherein the repositioned fastening tab acts as a marker for cutting the respective strap to a desired size, and cutting excess strap material that extends laterally beyond the repositioned fastening tab to provide a customized fit. The fitting method further may include repositioning the at least one fastening tab on the respective strap from a location on the first woven layer to a location on the second woven layer, thereby rendering the compression garment reversible. When the first woven layer has a first color, and the second woven layer has a second color different from the first color, the positioning of the fastening tab on either the first woven layer or the second woven layer is determinable of which color is visible when the compression garment is in the wrapped position.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more

DETAILED DESCRIPTION

Figure 1:
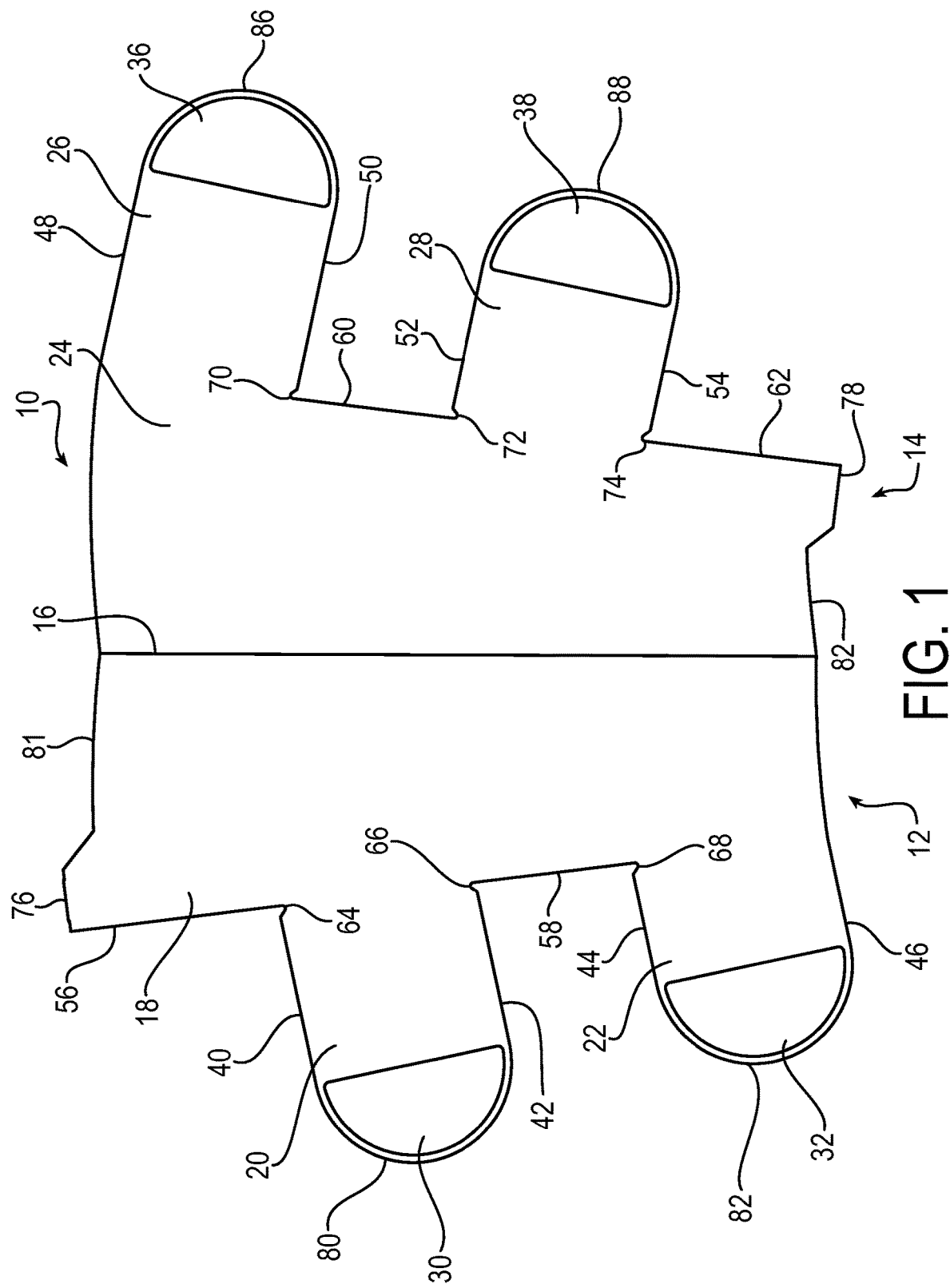
FIG. 1 is a drawing depicting a first configuration of exemplary components for use in a compression garment in accordance with embodiments of the present invention.

Embodiments of the present invention will now be described with reference to the drawings, wherein like reference numerals are used to refer to like elements throughout. It will be understood that the drawings are not necessarily to scale.

FIG. 1 is a drawing depicting a first configuration of exemplary components 10 for use in a compression garment in accordance with embodiments of the present invention. The components 10 essentially are depicted in a laid out position as would be oriented to form a compression garment. As further explained below, the components 10 would be sewn together to form the completed compression garment.

A compression garment that would be formed from the components 10 may be worn around a limb to prevent the build-up of fluid in the limb (edema). Persons who may use such a product include post-surgical patients, obese persons, and persons with ailments that impede circulation, such as Venous Disease or Lymphedema. Such a compression garment may improve circulation by compressing a limb or limb portion to prevent fluid from collecting in the lower limb portions, such as in the feet and ankles (leg compression garment) or hands (arm compression garment). The low-elastic compression garment generally is made of a stretch-limited material that provides high working pressures by limiting the amount of stretch in response to increased limb edema. In accordance with embodiments of the invention, the low-elastic compression garment is described as being configured as a leg compression garment worn essentially around a portion of a user's leg, and particularly the calf or thigh as typical examples. It will be appreciated, however, that that the features of the invention may be utilized in connection with a leg compression that extends from the calf over the knee to around the thigh, and/or going down to or around the foot and/or ankle. The precise size of the compression garment relative to the scope of the extension over the lower limb will depend upon the compression needs. It will further be appreciated that the features of the invention also may be utilized in connection with an arm compression garment that extends to any desired length over the arm and/or wrist or hand.

The components 10 for the compression garment may be formed of a first half 12 and a second half 14 that may be fixed together along a center line 16 where a seam can be formed when the two halves are sewn or otherwise fixed together (see additional details below). For purposes of definition, the longitudinal direction is defined as being substantially parallel to the direction by which the center line or seam extends. In addition, the lateral direction is the direction that is substantially perpendicular to the longitudinal direction. The term "substantially" is used because it will be appreciated that due to limb curvature, the center line and various edges of the compression garment may not be exactly straight. Rather, there may be a degree of slanting or curvature to the various edges of the compression garment components. Accordingly, references below to edges of the compression garment and components thereof as being either "lateral" or "longitudinal" denote a generalized direction allotting for any suitable slanting or curvature that may be present.

The first half 12 may include a first half main portion 18 and a plurality of straps that extend laterally from the first main portion. In the exemplary embodiment of FIG. 1, two straps 20 and 22 extend laterally from the first half main portion 18. Similarly, the second half 14 may include a second half main portion 24 and a plurality of straps that extend laterally from the second main portion. In the exemplary embodiment of FIG. 1, two straps 26 and 28 extend laterally from the second half main portion 24. When the two halves are fixed together, the first half main portion 18 and the second half main portion 24 together form a central main portion from which the straps laterally extend. It will be appreciated that the precise number of straps may vary depending upon the size of the compression garment relative to the scope of an amount of a limb portion that is desired to be wrapped for compression.

Once wrapped around a limb, the straps may be secured to an opposite half main portion by a fastening tab. As seen in the figures, each strap 20, 22, 26, and 28 respectively may have its own associated fastening tab 30, 32, 36, and 38. Any suitable fastening means may be employed, and mechanical fastening tabs are particularly suitable. For example, the fastening tabs may be hook-and-loop and similar type mechanical fastening elements. The straps may be pulled and secured to tension the straps in the wrapped position, resulting in a compression force being applied to the limb as described above.

In exemplary embodiments of the compression garment components 10, a length of the straps in a direction laterally extending from respective half main portions is approximately equal to the length in the lateral direction of the non-strap half main portions of the compression garment. The straps are staggered such that when the straps are wrapped around the remainder of the limb, there is an overlap of the lateral edges of adjacent straps in the wrapping around direction. Where each strap extends from the respective half main portion, a notch may be provided so that adjacent straps may overlap without bunching of the strap material.

Referring to FIG. 1, strap 20 has opposite lateral edges 40 and 42, strap 22 has opposite lateral edges 44 and 46, strap 26 has opposite lateral edges 48 and 50, and strap 28 has opposite lateral edges 52 and 54. In addition, the first half main portion 18 has longitudinal outer edges 56 and 58 that extend longitudinally between or adjacent to the straps 20 and 22. Similarly, the second half main portion 24 has longitudinal outer edges 60 and 62 that extend longitudinally between or adjacent to the straps 26 and 28. The lateral edges of the straps therefore extend substantially perpendicularly relative to the longitudinal outer edges of the half main portions. In other words, the plurality of straps extend laterally from the longitudinal outer edges of the central main portion formed when the two half main portions are fixed together.

In the example embodiment of FIG. 1, at least one notch may be provided adjacent to where a lateral edge of one of the straps meets one of the longitudinal outer edges of the central main portion. Accordingly, when the compression garment is in a wrapped position, lateral edges of adjacent straps that are associated with the at least one notch overlap. Referring to FIG. 1 as an exemplary configuration, for each strap, at least one notch is provided adjacent to where at least one lateral edge meets a corresponding longitudinal outer edge of a respective half main portion. As seen best in FIG. 1, for example, as to strap 20 a notch 64 is provided where lateral edge 40 meets longitudinal outer edge 56, and another notch 66 is provided where lateral edge 42 meets longitudinal outer edge 58. As to strap 22, a notch 68 is provided where lateral edge 44 meets longitudinal outer edge 58. As to strap 26, a notch 70 is provided where lateral edge 50 meets longitudinal outer edge 60. As to strap 28, a notch 72 is provided where lateral edge 52 meets longitudinal outer edge 60, and another notch 74 is provided where lateral edge 54 meets longitudinal outer edge 62.

The presence of the notches permits the straps to wrap around a limb portion with the lateral edges overlapping in a gapless configuration without bunching of the strap material as may occur in conventional configurations. In this example, strap 20 is associated with multiple opposite notches 64 and 66, and strap 28 is associated with multiple opposite notches 72 and 74, because straps 20 and 28 each extends between two adjacent straps in the wrapped position. In contrast, in this example straps 22 and 26 each are associated with only one notch (respectively notches 68 and 70) because straps 22 and 26 are the outer most straps in the wrapped configuration, having only one lateral edge adjacent to a lateral edge of another strap in the wrapped position. In such configuration, therefore, a notch is provided where a lateral edge of one of the straps meets one of the longitudinal outer edges of the central main portion, wherever a lateral edge of one of the straps overlaps a lateral edge of an adjacent strap when the compression garment is in the wrapped position. With such configuration, the straps are wrapped around a limb portion both without gaps between the straps, and without bunching of the strap material, resulting in an enhanced fit and comfort as compared to conventional configurations while maintaining full compression along the entirety of the compression garment.

Figure 2:
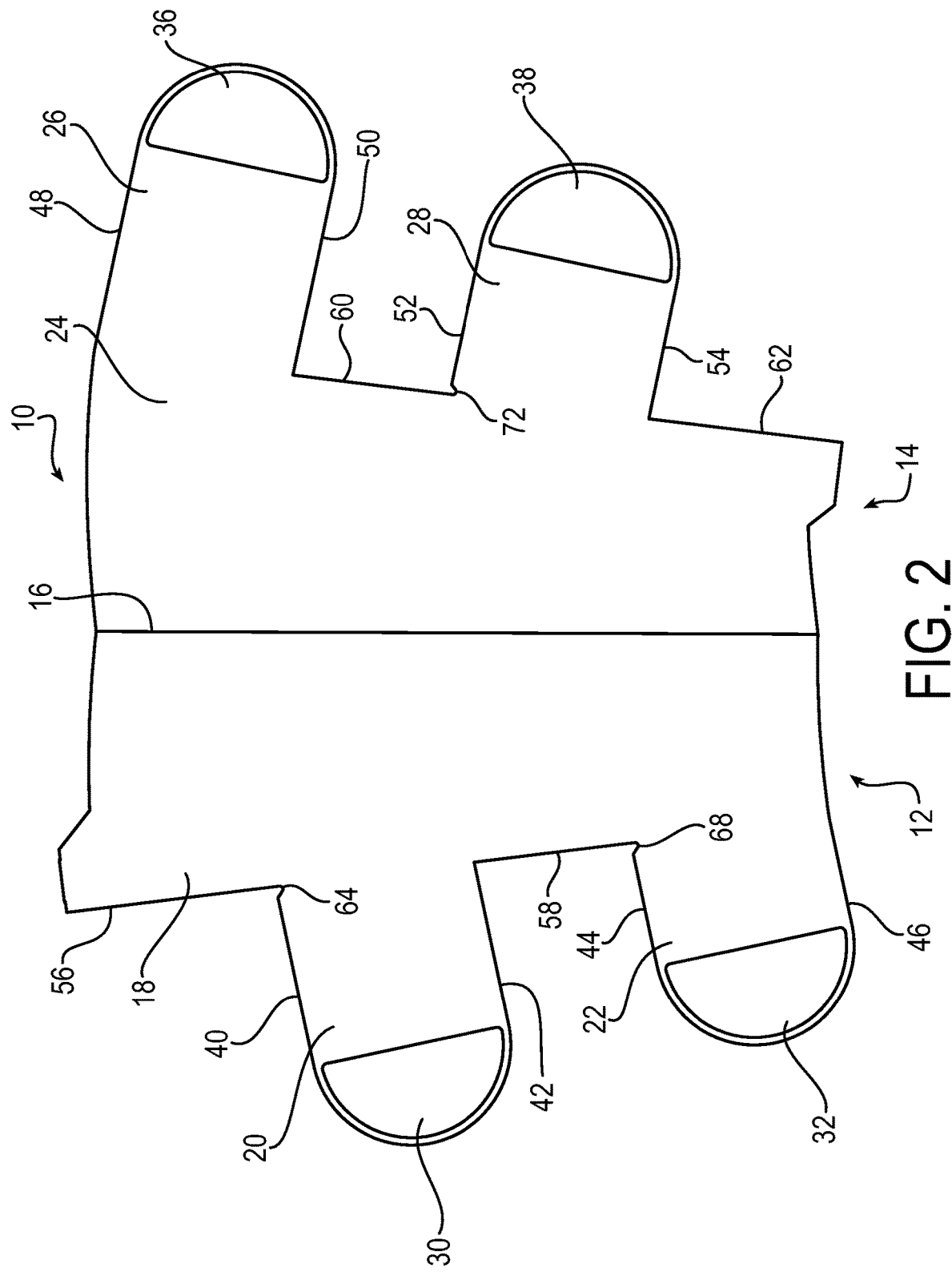
FIG. 2 is a drawing depicting a second configuration of exemplary components for use in a compression garment in accordance with embodiments of the present invention.

FIG. 2 is a drawing depicting a second configuration of exemplary components for use in a compression garment in accordance with embodiments of the present invention. As the configuration of FIG. 2 bears some similarity to the configuration of FIG. 1, like reference numerals are used for like components. Referring briefly to FIG. 2, such embodiment differs as to the precise configuration of the notches.

In the example of the embodiment of FIG. 2, as to strap 20 a notch 64 is provided where lateral edge 40 meets longitudinal outer edge 56, similarly as in the embodiment of FIG. 1. However, in contrast to the embodiment of FIG. 1, no notch is provided where lateral edge 42 meets longitudinal outer edge 58. As to strap 22, a notch 68 is provided where lateral edge 44 meets longitudinal outer edge 58, similarly as the embodiment of FIG. 1, but as to strap 26 in contrast to the embodiment of FIG. 1, no notch is provided where lateral edge 50 meets longitudinal outer edge 60. As to strap 28, a notch 72 is provided where lateral edge 52 meets longitudinal outer edge 60 similarly as the embodiment of FIG. 1, but in contrast to the embodiment of FIG. 1 no notch is provided where lateral edge 54 meets longitudinal outer edge 62.

The resultant configuration of FIG. 2, therefore, has fewer notches than the embodiment of FIG. 1. Specifically, there are half as many notches (three) in the embodiment of FIG. 2 as compared to the number of notches (six) in the embodiment of FIG. 1. This makes the embodiment of FIG. 3 somewhat easier to manufacture. Accordingly, instead of pairs of cooperating notches as depicted in FIG. 1, in the embodiment of FIG. 3 each notch 64, 68, and 72 interacts with an opposing straight portion of a lateral edge of an adjacent strap when the compression garment is in the wrapped position so as to form the overlapping region and provide the enhanced fit without bunching of the compression garment.

The notches in both the example embodiments of FIGS. 1 and 2 permit overlap of adjacent straps, but the amount of overlap is minimal as compared to conventional configurations, while still providing an effective gapless configurations. The amount of overlap may be ¼ inch or less, and may be as little as ⅛ inch. In this regard, the amount or degree of overlap is achieved regardless of the size of the compression garment. For example, a common amount of overlap may be present in a garment for a large limbed user and a small limbed user, and for a large limb (e.g., thigh garment) as compared to a small limb (e.g., calf or arm garment). Accordingly, the low-elastic compression garment is substantially less bulky as compared to conventional configurations. In addition, with the notches being located where the straps extend laterally from the half main portions, there is little tendency for the straps to move laterally relatively to each other. The present invention, therefore, provides a gapless configuration that has enhanced comfort and requires less material to manufacture.

The compression garment components may be made of a limited stretch material as are known in the art. In exemplary embodiments, the compression garment has three layers of material that are bonded together, including an internal compressible layer sandwiched between a first woven fabric layer and a second woven fabric layer. The internal compressible layer may be made of a synthetic rubber type material or the like, with neoprene being a suitable example. The woven fabric layers may be made of nylon loop type fabric materials or the like, with spandex materials being a suitable example.

The level of working pressure provided by the limited stretch nature of the material in part is dictated by the maximum stretch of the compression garment when worn as a property of the materials of the layers, and additionally the circumference of the limb of the user. The limb circumference in turn is a function of the degree of edema and muscle expansion and contraction, which may change with the changing condition of the user, or use conditions such as whether the user is resting or moving. Depending upon the degree by which the user stretches the compression garment around the given limb circumference, different levels of working pressure may be achieved. Typical radial compression or working pressure levels may run from about 20-60 mmHg depending upon the materials being used and the compression needs of the user. The low end of the range also would tend to be the pressure with the user at rest, whereas movement would tend to be associated with working pressures on the higher end of the range. In addition, the limited stretch material may be configured with different portions of the garment being capable of achieving different or graduated levels of compression along the garment.

As referenced above, one deficiency of conventional wrapped compression garments is that they can be difficult to don with sufficient compression, particularly for users who are elderly or infirmed. Referring again to FIG. 1, to render donning easier, the compression garment components 10 may include a distal counter pull tab 76 and a proximal counter pull tab 78. The distal and proximal counter pull tabs 76 and 78 are provided as extensions on opposite first and second lateral outer edges 81 and 82 of opposing half main portions 18 and 24. The lateral outer edges 81 and 82 extend substantially perpendicularly relative to the longitudinal outer edges of the central main portion. Accordingly, the distal counter pull tab 76 extends from the first lateral outer edge 81 of the central main portion, and the proximal counter pull tab 78 extends from the second lateral outer edge 82 of the central main portion.

When the compression garment is wrapped, the counter pull tabs 76 and 78 constitute dedicated gripping portions. When pulled by the user, the counter pull tabs 76 and 78 transmit the pulling forces in opposing directions to tension the straps, which aid the user in achieving the requisite tension on the straps. The compression garment, therefore, is easier to don as compared to conventional wrapped compression garments.

As referenced above, the compression garment components 10 may be formed of three layers including an internal compressible layer sandwiched between a first woven fabric layer and a second woven fabric layer. In exemplary embodiments, the first woven layer has a first color, and the second woven layer has a second color different from the first color (e.g., black and beige, although any colors may be employed), and the compression garment is reversible such that either color may be visible as desired by the user as follows.

As seen in the figures, each strap 20, 22, 26, and 28 respectively has an end 80, 82, 86, and 88 that is remote from where the strap meets the respective longitudinal outer edge of the central main portion. In exemplary embodiments, the ends may have a curved contour which provides for easier manipulation, and reduces tendencies of bunching or creasing of the material as could occur with end shapes having corners. Each curved end respectively may have an associated fastening tab 30, 32, 36, and 38 as referenced above that are provided at each of the ends of the straps. The fastening tabs also may have a curved contour so as to be shaped commensurately with the curved contour of the strap ends. As further explained below, each fastening tab may be removable from a respective strap and repositionable at a different location on the respective strap. The ability to remove and reposition the fastening tabs results in a compression garment that is both reversible and easily sized for a customized fit.

To provide reversibility, the fastening tabs are repositionable on the respective straps from a location on the first woven layer to a location on the second woven layer, thereby rendering the compression garment reversible. When the first woven layer has a first color, and the second woven layer has a second color different from the first color, the positioning of the fastening tab on either the first woven layer or the second woven layer is determinable of which color is visible when the compression garment is in a wrapped position. Accordingly, depending upon which side of the straps the fastening tabs are located, the compression garment may be wrapped in either direction, thereby permitting either color of woven fabric layers to be visible as desired by the user.

As referenced above, another deficiency of conventional compression garments is that they can be difficult to fit in a customized manner for different size users. The removability of the fastening tabs 30, 32, 36, and 38 permits easier customization as compared to conventional configurations. To customize the fit, each fastening tab may be removed and repositioned laterally on a same side along the respective straps at different lateral locations from the ends 80, 82, 86, and 88. By positioning the fastening tabs at different locations laterally along the straps relative to the strap ends, the repositioned fastening tabs act as a marker for cutting the straps to any suitable or desired size for a customized fit. In other words, once the fastening tabs are located at a desired position on the straps, any excess strap material that extends laterally beyond the repositioned fastening tabs may be cut away using the fastening tabs as a guide.

The present invention, therefore, includes a method of fitting a compression garment that is wrapped around a limb of a user. The fitting method may include the steps of providing the compression garment in accordance with any of the described embodiments (including any variations described below), removing at least one fastening tab from a respective strap, and repositioning the fastening tab at a different location on the respective strap.

The fitting method may include repositioning the at least one fastening tab laterally on a same side of the respective strap, wherein the repositioned fastening tab acts as a marker for cutting the respective strap to a desired size, and cutting excess strap material that extends laterally beyond the repositioned fastening tab to provide a customized fit. The fitting method further may include repositioning the at least one fastening tab on the respective strap from a location on the first woven layer to a location on the second woven layer, thereby rendering the compression garment reversible. When the first woven layer has a first color, and the second woven layer has a second color different from the first color, the positioning of the fastening tab on either the first woven layer or the second woven layer is determinable of which color is visible when the compression garment is in the wrapped position.

Figure 3:
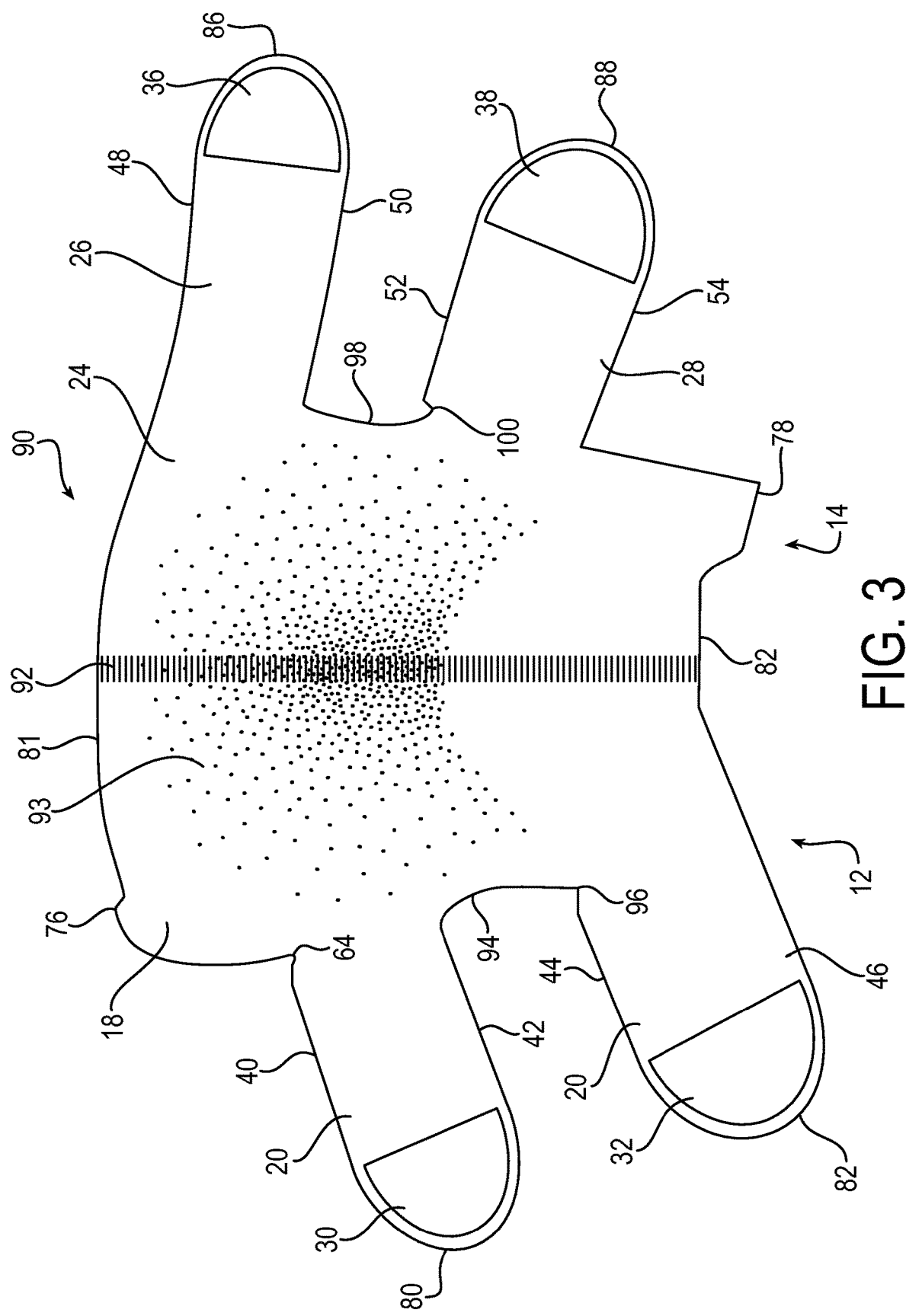
FIG. 3 is a drawing depicting a first exemplary compression garment in an unwrapped position in accordance with embodiments of the present invention.

FIG. 3 is a drawing depicting a first exemplary low-elastic, wrapped compression garment 90 in an unwrapped position in accordance with embodiments of the present invention. The compression garment 90 in one embodiment may be configured using the garment components 10 of FIG. 1 or 2. FIG. 3 includes certain modifications that are made to the components 10 to form the compression garment 90. As the configuration of the compression garment components of the compression garment 90 in FIG. 3 bears some similarity to the configuration of the components 10 of FIGS. 1 and 2, like reference numerals are used for like components.

Generally, FIG. 3 shows the compression garment components as the two garment halves 12 and 14 would be sewn or otherwise fixed together to form the complete compression garment 90. To fix the two halves 12 and 14 together, the two half main portions 18 and 24 may be sewn together, thereby forming a central seam 92 configured as a stitched central seam. The central main portion of the garment generally may therefore be considered a region of the of the compression garment substantially around and including the seam, and not including the straps. The seam is sewn with the stitched configuration to provide a biased curvature to the central main portion so that the central main portion of the completed garment is non-flat, i.e. the garment has a non-flat central region 93 with a curved contour in three dimensions that is intended to be commensurate with a typical shape of a limb portion, such as for example a typical calf for a lower leg compression garment. The biased nature into a three-dimensional, non-flat and curved central region is indicated by the shading in FIG. 3. The two half main portions 18 and 24 thus are joined together to form a curved central main portion that wraps around a substantial portion of the limb about the calf. The plurality of straps 20, 22, 26, and 28 extend laterally from the central main portion to wrap around the remainder of the limb.

The exemplary embodiment of FIG. 3 also has a different notch configuration relative to the previous embodiments, although the previous notch configurations likewise may also be employed in combination with a biased central seam. Generally, one or more of the longitudinal edges of at least one of the half main portions (which form the central main portion) may comprise a concave curvature extending between straps, and the notches are provided within one or more of such concave curvatures adjacent to where a strap extends from the central main portion. Referring to the example of FIG. 3, the longitudinal outer edge of the first half main portion 18 may be configured as a concave curvature 94 that is formed into such longitudinal outer edge extending between he straps 20 and 22. A notch 96 may be provided in the concave curvature 94 of the first half main portion 18, adjacent to where the strap 20 extends from the concave longitudinal outer edge 94. A similar notch configuration may be provided in relation to the second half main portion 24. In particular, the longitudinal outer edge of the second half main portion 24 may be configured as a concave curvature 98 that is formed into such longitudinal outer edge extending between he straps 26 and 28. A notch 100 may be provided in the concave curvature 98 of the second half main portion 24, adjacent to where the strap 26 extends from the concave longitudinal outer edge 98. In the example of FIG. 3, optionally the notch 64 also may be provided similarly as in the embodiment of FIG. 1.

Figure 4:
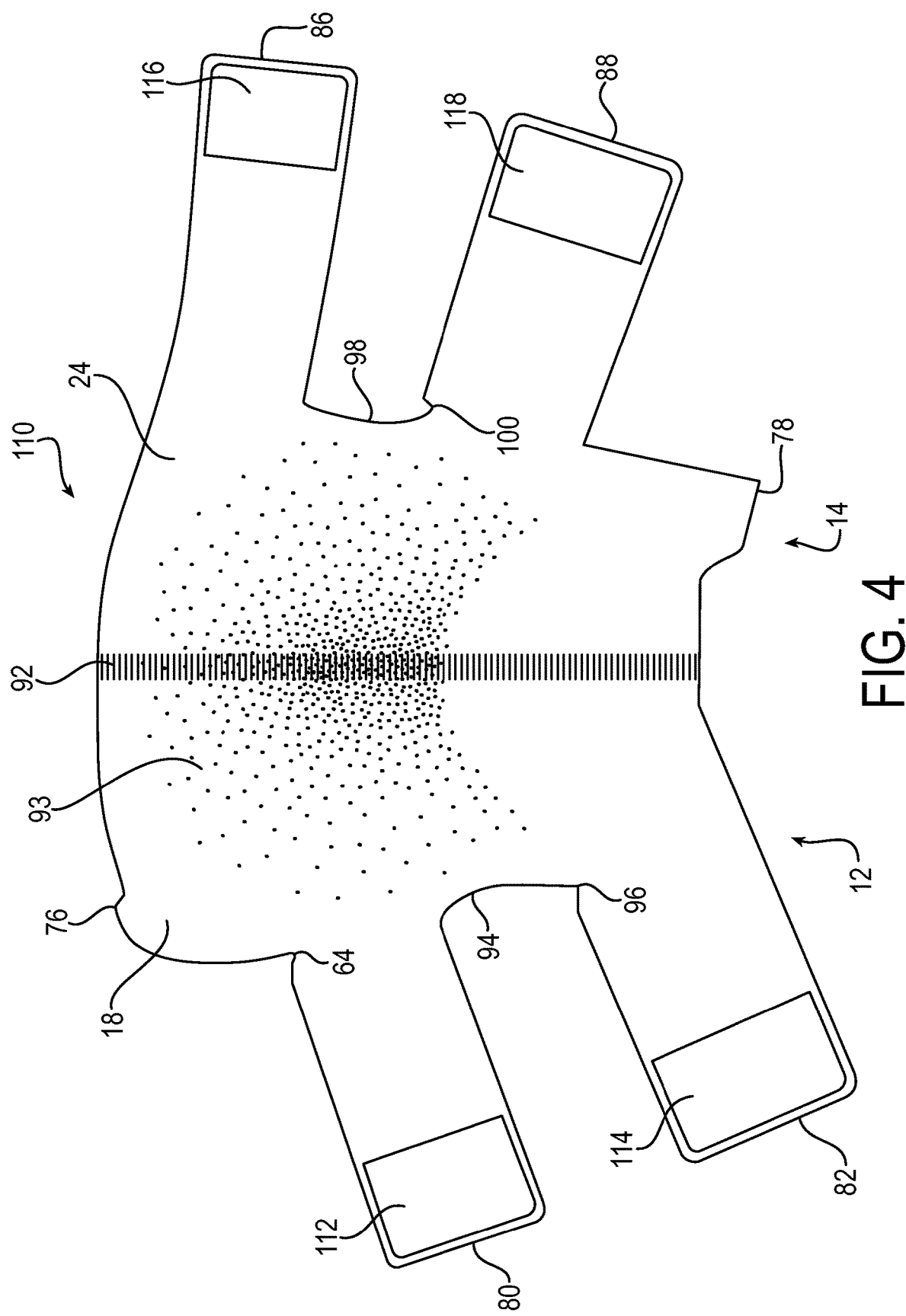
FIG. 4 is a drawing depicting a second exemplary compression garment in an unwrapped position in accordance with embodiments of the present invention.

FIG. 4 is a drawing depicting a second exemplary low-elastic, wrapped compression garment 110 in an unwrapped position in accordance with embodiments of the present invention. Again, as the configuration of the compression garment components of the compression garment 110 in FIG. 4 bears some similarity to the configuration of the components in the previous embodiments, like reference numerals are used for like components.

Generally, FIG. 4 shows the compression garment components as they would be sewn or otherwise fixed together to form the complete compression garment 110. Similarly as in the embodiment of FIG. 3, therefore, in the example of the compression garment 110 of FIG. 4, the two half main portions 18 and 24 may be sewn together, thereby forming the central seam 92 configured as a stitched central seam as above to provide a biased curvature in three dimensions to the resultant central main portion 93. In this manner, the completed garment has a non-flat central region or central main portion 93 with a curved contour in three dimensions that is intended to be commensurate with a typical shape of a limb portion, such as for example a typical calf for a lower leg compression garment. The biased nature into a three-dimensional, non-flat and curved central region is indicated again by the shading in FIG. 4. The exemplary embodiment of FIG. 4 has essentially the same notch configuration as the embodiment of FIG. 3, with at least one of the half main portions including a concave curvature (94, 98) extending between straps, and the notches 96 and 100 may be provided within the concave curvature adjacent to where a strap extends from the half main portion. In the example of FIG. 4, optionally the notch 64 also may be provided similarly as in the embodiment of FIG. 1.

The example of FIG. 4 differs from previous embodiments in the shapes of the strap ends 80, 82, 86, and 88. Such ends are shaped substantially in a rectangular fashion, and may have rounded corners insofar as referenced above, the curvature can provide for easier manipulation, and reduces tendencies of bunching or creasing of the material as could occur with end shapes having sharp corners. In this embodiment, fastening tabs 112, 114, 116, and 118 are shaped commensurately with the strap ends. Similarly as in previous embodiments, each fastening tab is removable from a respective strap and repositionable at a different location on the respective strap on either the same or opposite side. The ability to remove and reposition the fastening tabs again results in a compression garment that is both reversible and easily sized for a customized fit.

Figure 5:
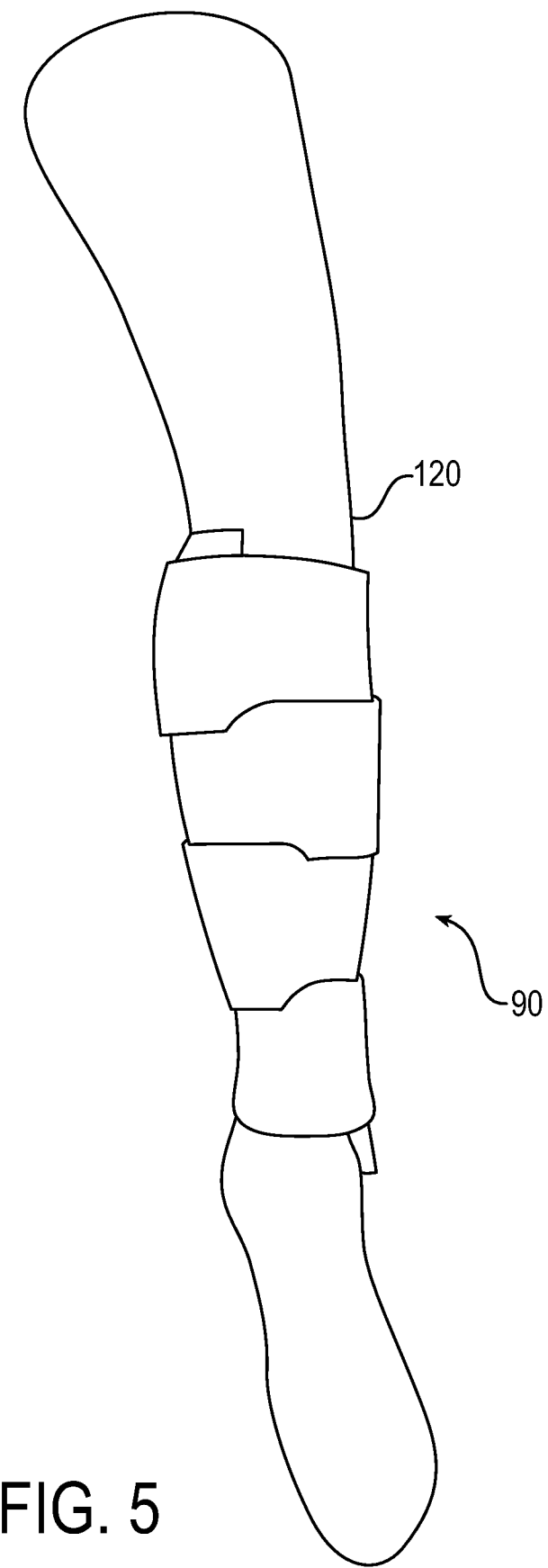
FIG. 5 is a drawing depicting an exemplary calf compression garment in use in accordance with embodiments of the present invention.

FIG. 5 is a drawing depicting an exemplary low-elastic, wrapped calf compression garment in use in a wrapped position wrapped around a limb portion 120 in accordance with embodiments of the present invention. In the example of FIG. 5, compression garment 90 is shown, although any of the compression garments or components thereof of the previous embodiments may be employed. The biased curvature of the non-flat central region described above permits a contoured fit commensurate with the curved shape of the calf. It further is shown that in the wrapped position, the notches permit the straps to be wrapped around a limb portion in an overlapping configuration both without gaps between the straps, and without bunching of the strap material, resulting in an enhanced fit and comfort as compared to conventional configurations while maintaining full compression along the entirety of the compression garment.

Figure 6:
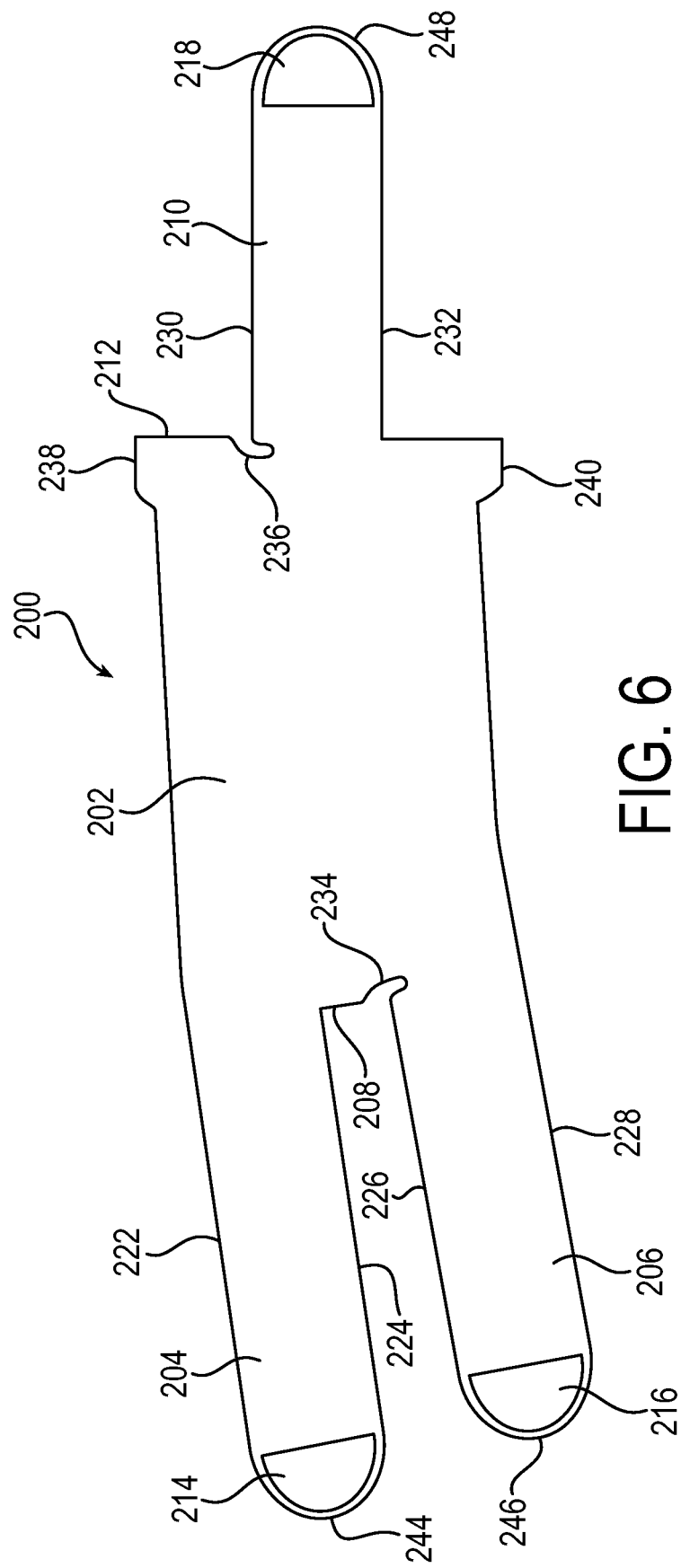
FIG. 6 is a drawing depicting a third exemplary compression garment in an unwrapped position in accordance with embodiments of the present invention.

FIG. 6 is a drawing depicting a third exemplary compression garment 200 in an unwrapped position in accordance with embodiments of the present invention. As further detailed below, the example embodiment of FIG. 6 may be particularly suitable for wrapping around an upper leg portion of a user, such as around the thigh area.

In the example of FIG. 6, the compression garment 200 may be formed as a seamless unitary component including the central main portion or region 202, rather than in two half main portions as in the previous embodiments, and the plurality of straps. Accordingly, there is no central seam as in the previous embodiments, as the unitary component comprises in combination the central main portion and the plurality of straps. The thigh circumference tends to be substantially larger and more uniform in curvature as compared to the calf. Accordingly, it is less desirable for a thigh garment to be configured with a biased seam in the compression garment, as a unitary component with a seamless main central portion provides for a better fit around the thigh.

A plurality of straps may extend laterally from the main portion. In the exemplary embodiment of FIG. 6, two straps 204 and 206 may be spaced apart from each other about a center axis of the garment and extend laterally from the central main portion 202 from a first longitudinal edge 208. In addition, a third strap 210 may extend from a second longitudinal edge 212 opposite from the first longitudinal edge. In such a three-strap configuration, the third strap 210 may extend from a more central location from the second longitudinal edge 212, such that in the wrapped position the third strap 210 extends between the two straps 204 and 206. It will be appreciated that the precise number of straps may vary depending upon the size of the compression garment relative to the scope of an amount of a limb portion that is desired to be wrapped for compression.

Once wrapped around a limb, the straps may be secured to an opposite end of the central main portion by a fastening tab. As seen in the figures, each strap 204, 206, and 210 respectively has its own associated fastening tab 214, 216, and 218. Similarly to previous embodiments, any suitable fastening means may be employed, and mechanical fastening tabs are particularly suitable. For example, the fastening tabs may be hook-and-loop and similar type mechanical fastening elements. The straps may be pulled and secured to tension the straps in the wrapped position, resulting in a compression force being applied to the limb as described above.

In the exemplary embodiment of the compression garment 200, a length of the straps in a direction laterally extending from the main portion is approximately equal to the length in the lateral direction of the non-strap main portion of the compression garment. The straps are staggered such that when the straps are wrapped around the remainder of the limb, there is an overlap of the lateral edges of adjacent straps in the wrapping around direction. Similarly as in the previous embodiments, a notch configuration may be provided so that adjacent straps may overlap without bunching of the strap material. Any of the notch configurations used with respect to the previous embodiments likewise may also be employed in combination with a unitary central main portion that may be employed for a thigh compression garment.

Referring to FIG. 6, strap 204 has opposite lateral edges 222 and 224, strap 206 has opposite lateral edges 226 and 228, and strap 210 has opposite lateral edges 230 and 232. The lateral edges are essentially perpendicular to the longitudinal edges 208 and 212 such that the plurality of straps extend laterally from the longitudinal outer edges of the main portion 202.

FIG. 6 shows another example of a notch configuration (which also may be used in connection with any of the previous embodiments). In the example embodiment of FIG. 6, the notches may be configured as shaped recesses formed extending into the central main portion adjacent to where a strap extends from the central main portion. Referring to FIG. 6, a first shaped notch 234 may be formed in the main portion 202 adjacent to where the strap 206 extends from the main portion near the lateral edge 226. Similarly, a second shaped recess notch 236 may be formed in the main portion 202 adjacent to where the third strap 210 extends from the main portion at the lateral edge 230. In this particular example, the notches are rounded indentations into the main portion 202, although any suitable shaped notches may be employed. Optionally, additional notches may be provided, and the notch shapes may be the same or different from each other. For example, a comparable notch may be formed in the main portion 202 adjacent to where the strap 204 extends from the main portion at its lateral edge 224, and/or another notch may be formed in the main portion 202 adjacent to where the strap 210 extends from the main portion at the lateral edge 232 opposite from the notch 236. Accordingly, when the compression garment is in a wrapped position, lateral edges of adjacent straps that are associated with the at least one notch overlap similarly as in previous embodiments. The presence of the notches thus permits the straps to wrap around a limb portion, and particularly a thigh portion in this example, with the lateral edges overlapping in a gapless configuration without bunching of the strap material as may occur in conventional configurations, while maintaining full compression along the entirety of the compression garment.

The thigh garment of FIG. 6 also may include pull tabs to aid in donning the garment. For example, the compression garment 200 may include a distal counter pull tab 238 and a proximal counter pull tab 240. The distal and proximal counter pull tabs 238 and 240 are provided as extensions from the main portion 202. Similarly as in previous embodiments, when the compression garment is wrapped, the counter pull tabs 238 and 240 constitute dedicated gripping portions. When pulled by the user, the counter pull tabs 238 and 240 transmit the pulling forces in opposing directions to tension the straps, which aids the user in achieving the requisite tension on the straps. The compression garment, therefore, is easier to don as compared to conventional wrapped compression garments.

As seen in the figures, each strap 204, 206, and 210 respectively may have an end 244, 246, and 248 that is remote from where the strap meets the respective longitudinal outer edge of the main portion. Similarly to the embodiments of FIGS. 1 and 2, the ends may have a curved contour which provides for easier manipulation, and reduces tendencies of bunching or creasing of the material as could occur with end shapes having corners. Each curved end respectively may have the associated fastening tab 214, 216, and 218 similarly as previous embodiments, which are removable from a respective strap and repositionable at a different location on either side of the respective strap so that the garment again is both reversible and easily sized for a customized fit. To customize the fit, each fastening tab may be removed and repositioned laterally on a same side along the respective straps at different lateral locations from the ends 244, 246, and 248. By positioning the fastening tabs at different locations laterally along the straps relative to the strap ends, the repositioned fastening tabs act as a marker for cutting the straps to any suitable or desired size for a customized fit. By repositioning the fastening tabs on the opposite side of the respective strap, the compression garment is made reversible.

Figure 7:
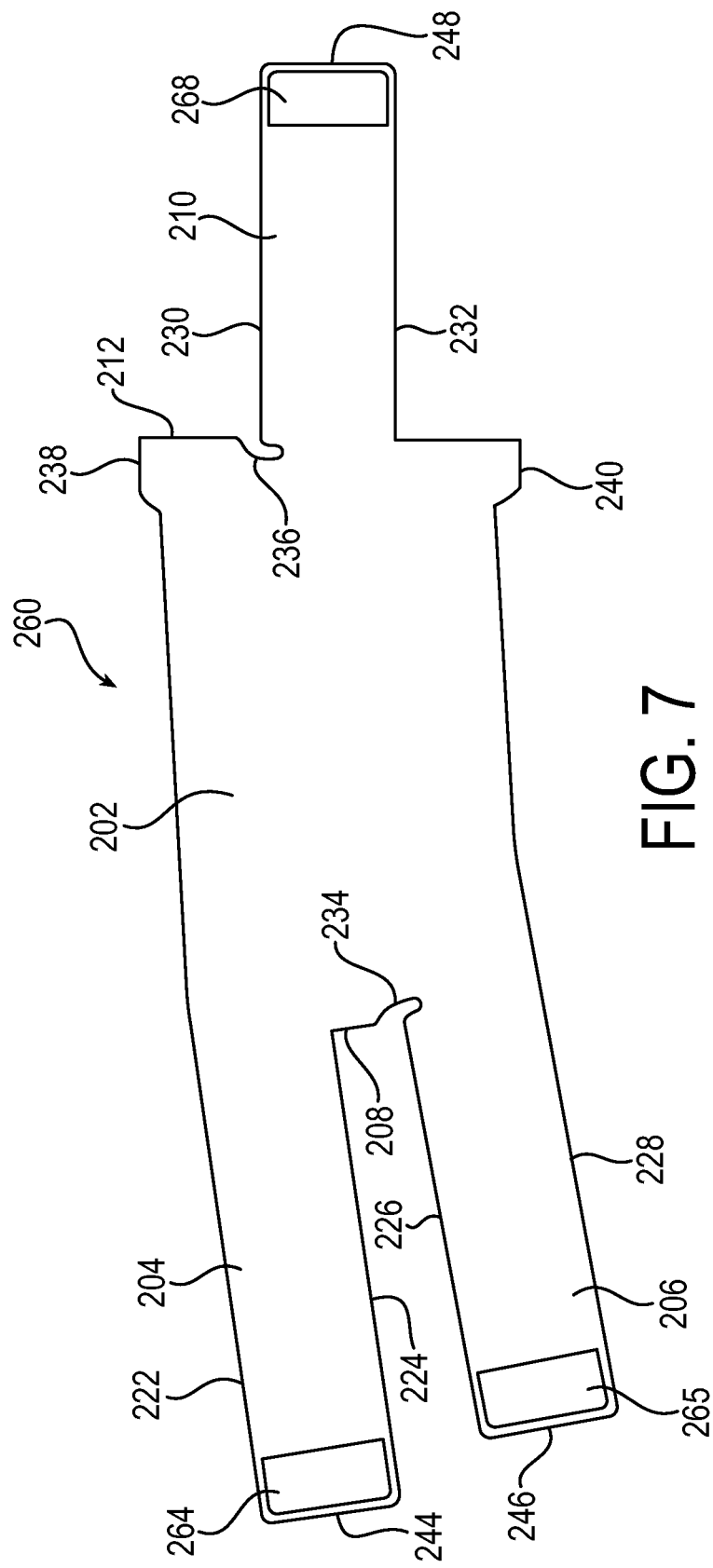
FIG. 7 is a drawing depicting a fourth exemplary compression garment in an unwrapped position in accordance with embodiments of the present invention.

FIG. 7 is a drawing depicting a second exemplary compression garment 260 in an unwrapped position in accordance with embodiments of the present invention. Compression garment 260 is a variation of the thigh compression garment 200 of FIG. 6. Accordingly, the configuration of the compression garment 260 bears some similarity to the configuration of the compression garment 200, so like reference numerals are used for like components in FIGS. 6 and 7.

The example of FIG. 7 differs from the previous embodiment of FIG. 6 largely in the shapes of the strap ends 244, 246, and 248. As to such features, the embodiment of FIG. 6 is similar to that of FIG. 4. The strap ends may be shaped substantially in a rectangular fashion, and may have rounded corners insofar as referenced above, the curvature can provide for easier manipulation, and reduces tendencies of bunching or creasing of the material as could occur with end shapes having sharp corners. In this embodiment, fastening tabs 264, 265, and 268 are shaped commensurately with the strap ends. Similarly as in previous embodiments, each fastening tab is removable from a respective strap and repositionable at a different location on either side of the respective strap. The ability to remove and reposition the fastening tabs again results in a compression garment that is both reversible and easily sized for a customized fit.

Figure 8:
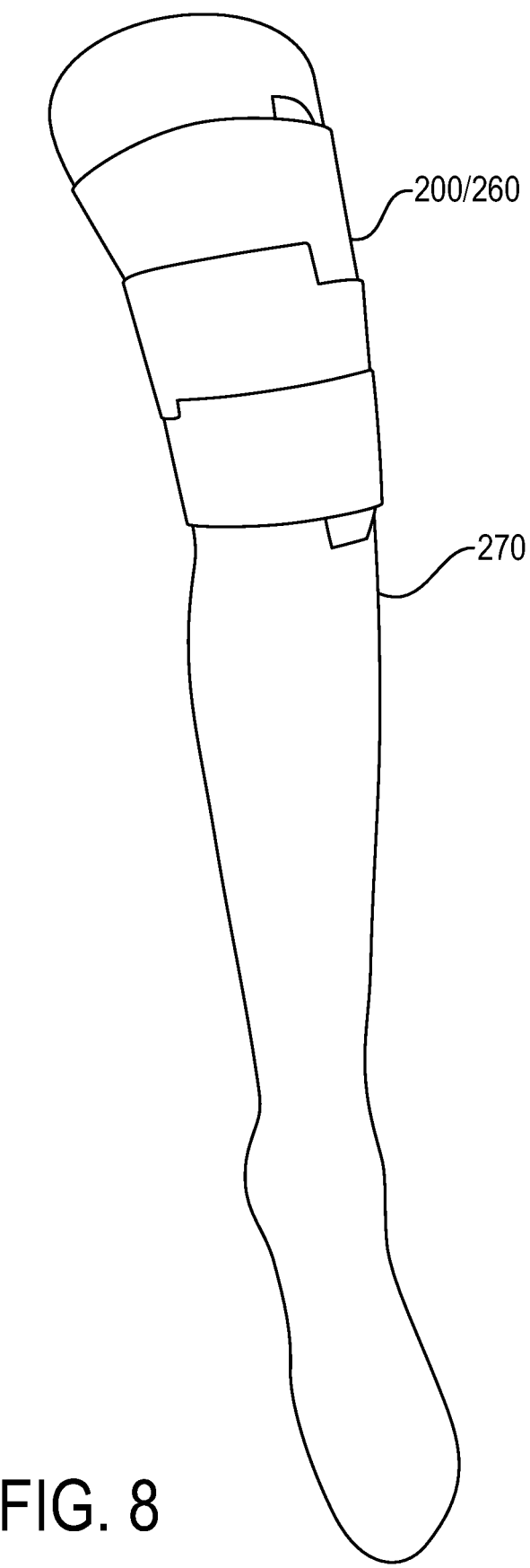
FIG. 8 is a drawing depicting an exemplary thigh compression garment in use in accordance with embodiments of the present invention.

FIG. 8 is a drawing depicting an exemplary low-elastic, wrapped thigh compression garment such as garment 200 or 260, in use in a wrapped position wrapped around a limb portion 270 in accordance with embodiments of the present invention. In the wrapped position, the notches permit the straps to be wrapped around a limb portion in an overlapping configuration both without gaps between the straps, and without bunching of the strap material, resulting in an enhanced fit and comfort as compared to conventional configurations while maintaining full compression along the entirety of the compression garment.

An aspect of the invention, therefore, is a low-elastic, wrapped compression garment that is to be wrapped around a limb of a user. In exemplary embodiments, the low-elastic compression includes a central main portion including a plurality of longitudinal outer edges, a plurality of straps that extend laterally from the longitudinal outer edges of the central main portion, each of the plurality of straps having opposite lateral edges, and at least one notch adjacent to where a lateral edge of one of the straps meets one of the longitudinal outer edges of the central main portion. When the compression garment is in a wrapped position, lateral edges of adjacent straps that are associated with the at least one notch can overlap. The low-elastic compression garment may include one or more of the following features, either individually or in combination.

In an exemplary embodiment of the compression garment, the at least one notch includes a plurality of notches. A notch is provided where a lateral edge of one of the straps meets one of the longitudinal outer edges of the central main portion, wherever a lateral edge of one of the straps overlaps a lateral edge of an adjacent strap when the compression garment is in the wrapped position.

In an exemplary embodiment of the compression garment, the at least one notch includes a plurality of notches. Each notch is provided where a lateral edge of one of the straps meets one of the longitudinal outer edges of the central main portion, and each notch interacts with an opposing straight portion of a lateral edge of an adjacent strap when the compression garment is in the wrapped position.

In an exemplary embodiment of the compression garment, at least one of the plurality of longitudinal edges of the central main portion comprises a concave curvature extending between straps, and a notch is provided within the concave curvature adjacent to where a strap extends from the central main portion.

In an exemplary embodiment of the compression garment, more than one of the plurality of longitudinal edges of the central main portion comprises a concave curvature extending between straps, and a notch is provided within each of the concave curvatures adjacent to where a strap extends from the central main portion.

In an exemplary embodiment of the compression garment, the at least one notch comprises a shaped recess formed extending into the central main portion adjacent to where a strap extends from the central main portion.

In an exemplary embodiment of the compression garment, the at least one notch comprises a plurality of notches, wherein each notch comprises a shaped recess formed extending into the central main portion adjacent to where a strap extends from the central main portion.

In an exemplary embodiment of the compression garment, the plurality of notches comprises at least two notches configured as rounded indentations that extend into the central main portion.

In an exemplary embodiment of the compression garment, an amount of overlap of lateral edges of adjacent straps is ¼ inch or less.

In an exemplary embodiment of the compression garment, an amount of overlap of lateral edges of adjacent straps is between ⅛ inch and ¼ inch.

In an exemplary embodiment of the compression garment, the compression garment comprises a first half and a second half that are fixed together at a central seam, the central main portion being a region of the compression garment around the central seam not including the straps.

In an exemplary embodiment of the compression garment, the first and second halves are sewn together to configure the central seam as a stitched central seam.

In an exemplary embodiment of the compression garment, the central seam provides a biased curvature to the central main portion, wherein the central main portion is non-flat.

In an exemplary embodiment of the compression garment, the compression garment is formed as a seamless unitary component including the central main portion and the plurality of straps.

In an exemplary embodiment of the compression garment, the low-elastic compression garment includes a central main portion including a plurality of longitudinal outer edges, and first and second opposite lateral outer edges that extend substantially perpendicularly relative to the longitudinal outer edges, a plurality of straps that extend laterally from the longitudinal outer edges of the central main portion, and a distal counter pull tab that extends from the first lateral outer edge of the central main portion, and a proximal counter pull tab that projects from the second lateral outer edge of the central main portion. When the distal and proximal counter pull tabs are pulled by the user, pulling forces are transmitted in opposing directions to tension the straps.

In an exemplary embodiment of the compression garment, the low-elastic compression garment includes a central main portion including a plurality of longitudinal outer edges, a plurality of straps that extend laterally from the longitudinal outer edges of the central main portion, each of the plurality of straps having an end that is remote from where the strap meets the longitudinal outer edge of the central main portion, and a plurality of fastening tabs respectively provided at each of the ends of the straps, wherein each fastening tab is removable from a respective strap and repositionable at a different location on the respective strap.

In an exemplary embodiment of the compression garment, the fastening tabs are repositionable laterally on a same side of the respective straps, wherein a repositioned fastening tab acts as a marker for cutting the respective strap to a desired size.

In an exemplary embodiment of the compression garment, the strap ends have a curved contour, and the fastening tabs have a curved contour that is commensurate with the curved contour of the strap ends.

In an exemplary embodiment of the compression garment, the compression garment comprises three layers of material including an internal compressible layer between a first woven layer and a second woven layer; and the fastening tabs are repositionable on the respective straps from a location on the first woven layer to a location on the second woven layer, thereby rendering the compression garment reversible.

In an exemplary embodiment of the compression garment, the first woven layer has a first color, and the second woven layer has a second color different from the first color, and the positioning of the fastening tab on either the first woven layer or the second woven layer is determinable of which color is visible when the compression garment is in a wrapped position.

In an exemplary embodiment of the compression garment, the central main portion further includes first and second opposite lateral outer edges that extend substantially perpendicularly relative to the longitudinal outer edges. The compression garment further includes a distal counter pull tab that extends from the first lateral outer edge of the central main portion, and a proximal counter pull tab that extends from the second lateral outer edge of the central main portion, wherein when the distal and proximal counter pull tabs are pulled by the user, pulling forces are transmitted in opposing directions to tension the straps.

In an exemplary embodiment of the compression garment, each of the plurality of straps has an end that is remote from where the strap meets the longitudinal outer edge of the central main portion, and a plurality of fastening tabs respectively are provided at each of the ends of the straps, wherein each fastening tab is removable from a respective strap and repositionable at a different location on the respective strap.

In an exemplary embodiment of the compression garment, the fastening tabs are repositionable laterally on a same side of the straps, wherein the repositioned fastening tab acts as a marker for cutting the respective strap to a desired size.

In an exemplary embodiment of the compression garment, the strap ends have a curved contour, and the fastening tabs have a curved contour that is commensurate with the curved contour of the strap ends.

In an exemplary embodiment of the compression garment, the compression garment comprises three layers of material including an internal compressible layer between a first woven layer and a second woven layer, and the fastening tabs are repositionable on the straps from a location on the first woven layer to a location on the second woven layer, thereby rendering the compression garment reversible.

In an exemplary embodiment of the compression garment, the first woven layer has a first color, and the second woven layer has a second color different from the first color, and the positioning of the fastening tab on either the first woven layer or the second woven layer is determinable of which color is visible when the compression garment is in a wrapped position.

In an exemplary embodiment of the compression garment, the compression garment comprises a first half and a second half that are fixed together at a central seam.

In an exemplary embodiment of the compression garment, the first and second halves are sewn together to configure the central seam as a stitched central seam.

In an exemplary embodiment of the compression garment, the central seam provides a biased curvature to the central main portion.

In an exemplary embodiment of the compression garment, the first half comprises a first half main portion and a portion of the straps that extend laterally from the first half main portion, and the second half comprises a second half main portion and another portion of the straps that extend laterally from the second half main portion, and a length of the straps extending from the half main portions is approximately equal to a length of the half main portions in the lateral direction.

In an exemplary embodiment of the compression garment, each strap has a distal end that attaches to the central main portion in the wrapped position, whereby the compression garment applies a working pressure to a limb to provide limb compression when the compression garment is in the wrapped position.

Another aspect of the invention is a method of fitting a compression garment that is wrapped around a limb of a user. In exemplary embodiments, the fitting method Includes the steps of: providing a compression garment in accordance with any of the above embodiments, the compression garment including a plurality of removable fastening tabs respectively provided at each of the ends of the straps; removing at least one fastening tab from a respective strap; and repositioning the fastening tab at a different location on the respective strap. The fitting method may include one or more of the following features, either individually or in combination.

In an exemplary embodiment of the fitting method, the fitting method further includes, repositioning the at least one fastening tab laterally on a same side of the respective strap, wherein the repositioned fastening tab acts as a marker for cutting the respective strap to a desired size; and cutting excess strap material that extends laterally beyond the repositioned fastening tab.

In an exemplary embodiment of the fitting method, the compression garment comprises three layers of material including an internal compressible layer between a first woven layer and a second woven layer; and the fitting method further comprises repositioning the at least one fastening tab on the respective strap from a location on the first woven layer to a location on the second woven layer, thereby rendering the compression garment reversible.

In an exemplary embodiment of the fitting method, the first woven layer has a first color, and the second woven layer has a second color different from the first color, and the positioning of the fastening tab on either the first woven layer or the second woven layer is determinable of which color is visible when the compression garment is in a wrapped position.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A compression garment that is to be wrapped around a limb of a user, the compression garment comprising:
   a central main portion including a plurality of longitudinal outer edges;
   a plurality of straps that extend laterally and perpendicularly from the plurality of longitudinal outer edges of the central main portion, each of the plurality of straps having an end that is formed by a curved contour and that is remote from where each strap meets a longitudinal outer edge of the plurality of longitudinal outer edges of the central main portion; and
   a plurality of fastening tabs respectively provided at each of the ends of the plurality of straps, wherein each fastening tab is removable from its respective strap and repositionable at a different location on the respective strap;
   wherein the compression garment comprises three layers of material including an internal compressible layer between a first woven layer and a second woven layer;
   the plurality of fastening tabs are secured to the first woven layer on the respective straps with a mechanical fastener that holds the plurality of fastening tabs on the respective straps in a manner that enables the plurality of fastening tabs to be removed from a first location on the first woven layer to a second location on the second woven layer, thereby rendering the compression garment adapted to be reversible on the limb, wherein each of the plurality of fastening tabs are removably positioned such that it has a curved contour commensurate with and not extending beyond the curved contour of each strap end; and
   wherein the first woven layer has a first color, and the second woven layer has a second color different from the first color, and a positioning of the plurality of fastening tabs on either the first woven layer or the second woven layer is determinable of which color is visible when the compression garment is in a wrapped position on the limb.

2. The compression garment of claim 1, wherein the compression garment comprises a first half and a second half that are fixed together at a central seam, the central main portion being a region of the compression garment around the central seam not including the plurality of straps.

3. The compression garment of claim 2, wherein the first and second halves are sewn together such that the central seam is a stitched central seam.

4. The compression garment of claim 3, wherein the central seam provides a biased curvature to the central main portion, wherein the central main portion is non-flat.

5. The compression garment of claim 2, wherein:
   the first half comprises a first half main portion and a portion of the plurality of straps that extend laterally from the first half main portion, and the second half comprises a second half main portion and another portion of the plurality of straps that extend laterally from the second half main portion; and
   a length of the plurality of straps extending from each half main portion is approximately equal to a length of each half main portion in the lateral direction.

6. The compression garment of claim 1, wherein the plurality of fastening tabs are repositionable laterally on a same side of the respective straps, wherein a repositioned fastening tab of the plurality of fastening tabs is configured to act as a marker for cutting the respective strap to a desired size.

7. The compression garment of claim 1, wherein the compression garment is formed as a seamless unitary component including the central main portion and the plurality of straps.

* * * * *

UNITED STATES PATENT AND TRADEMARK OFFICE
CERTIFICATE OF CORRECTION

PATENT NO. : 11,246,764 B2  
APPLICATION NO. : 15/580840  
DATED : February 15, 2022  
INVENTOR(S) : Greg Biddulph et al.

It is certified that error appears in the above-identified patent and that said Letters Patent is hereby corrected as shown below:

On the Title Page

Item (73), "Julius Zom. Inc." should read --Julius Zorn, Inc.--

Signed and Sealed this
Nineteenth Day of April, 2022

Katherine Kelly Vidal
*Director of the United States Patent and Trademark Office*